US012704449B2

(12) United States Patent
Brown et al.

(10) Patent No.: US 12,704,449 B2
(45) Date of Patent: Aug. 11, 2026

(54) SYSTEMS, APPARATUSES, AND METHODS TO MEASURE DEFORMABILITY OF RED BLOOD CELLS IN MICROFLUIDIC CHANNELS

(71) Applicants: Honeywell International Inc., Charlotte, NC (US); Emory University, Atlanta, GA (US)

(72) Inventors: Andy W Brown, Richardson, TX (US); Moin S Shafai, Richardson, TX (US); Ryadh A Zakaria, Portsmouth (GB); Christina Caruso, Atlanta, GA (US); Evelyn Kendall Williams, Atlanta, GA (US); Kirby Fibben, Atlanta, GA (US); Wilbur Lam, Decatur, GA (US)

( * ) Notice: Subject to any disclaimer, the term of this patent is extended or adjusted under 35 U.S.C. 154(b) by 290 days.

(21) Appl. No.: 18/542,078

(22) Filed: Dec. 15, 2023

(65) Prior Publication Data

US 2025/0198897 A1 Jun. 19, 2025

(51) Int. Cl.
*G01N 15/01* (2024.01)
*B01L 3/00* (2006.01)
(Continued)

(52) U.S. Cl.
CPC ........ *G01N 15/01* (2024.01); *B01L 3/502761* (2013.01); *G01N 15/1434* (2013.01); *G06T 7/0012* (2013.01); *G06T 7/20* (2013.01); *G16H 10/40* (2018.01); *G16H 15/00* (2018.01); *B01L 2200/0663* (2013.01);
(Continued)

(58) Field of Classification Search
CPC ... G06K 9/00; C07K 14/70525; G01N 15/147
USPC ....... 382/100, 103, 106, 128–134, 155, 162, 382/168, 173, 181, 254, 276, 305, 312; 378/6, 41, 42
See application file for complete search history.

(56) References Cited

U.S. PATENT DOCUMENTS 9,007,433 B2 4/2015 Ozcan et al.
9,341,636 B2 5/2016 Poher et al.
(Continued)

OTHER PUBLICATIONS

Combining optical diffraction tomography with imaging flow cytometry for characterizing morphology, hemoglobin content, Yu-Hsiang Chang, 1 (Year: 2023).*
(Continued)

*Primary Examiner* — Seyed H Azarian
(74) *Attorney, Agent, or Firm* — Alston & Bird LLP

(57) ABSTRACT

A system and a method for measuring deformability of red blood cells in microfluidic channels are disclosed. The system comprises one or more devices having one or more microfluidic channels with at least one cross-sectional dimension and configured to allow deformation of red blood cells of a blood sample to flow through the one or more microfluidic channels. Further, at least one imager is configured to generate a sequence of digital holography images or videos of the red blood cells of the blood sample transiting through the one or more microfluidic channels. Further, the system includes at least one processor that is operationally coupled to the at least one imager. The at least one processor is configured to analyze the generated sequence of digital holography images or videos to quantify and characterize deformability of the red blood cells within the one or more microfluidic channels.

20 Claims, 14 Drawing Sheets

(51) Int. Cl.

| | |
|---|---|
| ***G01N 15/1434*** | (2024.01) |
| ***G06K 9/00*** | (2022.01) |
| ***G06T 7/00*** | (2017.01) |
| ***G06T 7/20*** | (2017.01) |
| ***G16H 10/40*** | (2018.01) |
| ***G16H 15/00*** | (2018.01) |

(52) U.S. Cl.

CPC . *B01L 2300/0654* (2013.01); *B01L 2300/087* (2013.01); *G01N 2015/012* (2024.01); *G06T 2207/10016* (2013.01); *G06T 2207/10056* (2013.01); *G06T 2207/30024* (2013.01)

(56) References Cited

U.S. PATENT DOCUMENTS

| | | | | |
|---|---|---|---|---|
| 10,843,922 | B2 | 11/2020 | Lagae et al. | |
| 11,493,428 | B2 * | 11/2022 | Grisham | B01L 3/502776 |
| 2017/0061619 | A1 * | 3/2017 | Lagae | G01N 15/147 |
| 2017/0227495 | A1 * | 8/2017 | Gurkan | G01N 33/49 |
| 2020/0116617 | A1 * | 4/2020 | Singh | G03H 1/0866 |
| 2021/0032588 | A1 * | 2/2021 | Masaeli | B01L 3/502761 |
| 2022/0404334 | A1 * | 12/2022 | Gurkan | C07K 14/70525 |
| 2023/0184657 | A1 | 6/2023 | Brown et al. | |
| 2023/0221239 | A1 | 7/2023 | Praljak et al. | |
| 2023/0326047 | A1 | 10/2023 | Brown et al. | |
| 2024/0091761 | A1 | 3/2024 | Myers | |
| 2024/0110858 | A1 | 4/2024 | Kishore et al. | |

OTHER PUBLICATIONS

Chang et al., “Combining optical diffraction tomography with imaging flow cytometry for characterizing morphology, hemoglobin content, and membrane deformability of live red blood cells”, arXiv preprint arXiv: Sep. 26, 2023, XP091623782.

Extended European Search Report Mailed on Apr. 14, 2025 for EP Application No. 24217030, 11 page(s).

Grigorev et al., “Advances in microfluidics for single red blood cell analysis”, Biosensors, vol. 13, No. 1, Jan. 9, 2023, pp. 117.

Guruprasad et al., “Integrated automated particle tracking microfluidic enables high-throughput cell deformability cytometry for red cell disorders”, American journal of hematology, vol. 94, No. 2, Nov. 28, 2019, pp. 189-199.

Matthews et al., “Technologies for measuring red blood cell deformability”, Lab on a Chip, vol. 22, No. 7, Mar. 29, 2022, pp. 1254-1274.

Biochip Labs, “Comprehensive & Functional Biomarker Assays for Blood Testing”, retrieved from the Internet at URL: <https://biochiplabs.com/> on Aug. 27, 2024, 4 pages.

Cytovale, “IntelliSep”, retrieved from the Internet at URL: <https://cytovale.com/> on Sep. 5, 2024, 3 pages.

Functional Fluidics, “Functional Fluidics Defining Red Blood Cell Health”, retrieved from the Internet at URL: <https://www.functionalfluidics.com/> on Aug. 27, 2024, 5 pages.

Holmarc, “Digital Inline Holography Microscope”, retrieved from the Internet at URL: <https://www.holmarc.com/dihm. php? on Aug. 27, 2024, 2 pages.

iClots, “General information about iCLOTS”, retrieved from the Internet at URL: < https://iclots.readthedocs.io/en/latest/general_information.html> on Sep. 5, 2024, 5 pages.

IMEC-INT, “Lens-free imaging microscopes”, retrieved from the Internet at URL: <https://web.archive.org/web/20230205183049/https://www.imec-int.com/en/lens-free-microscopy> on Aug. 27, 2024, 3 pages.

Kaligaselvi Lenin et al., U.S. Patent Application No. 18/602, 175 for “Laser Calibration and Stabilization Algorithm for Microscopy Device”, filed Mar. 12, 2024.

Ryadh Abdullah Zakaria et al., U.S. Appl. No. 18/460,328 for “Imaging Device With a Photonic Integrated Circuit”, filed Sep. 1, 2023.

Sigtuple, “The Future of Microscopy is Here”, retrieved from the Internet at URL: < https://sigtuple.com/> on Aug. 27, 2024, 5 pages.

Vittorio Bianco et al., “Imaging adherent cells in the microfluidic channel hidden by flowing RBCs as occluding objects by a holographic method,” Lab Chip, 14:2499-2504, (Apr. 2014). [Retrieved from the Internet Apr. 22, 2024: URL: <https://www.researchgate.net/publication/262291426_Imaging_adherent_cell_in_microfluidic_channel_hidden_by_flowing_RBCs_as_occluding_obje cts_by_holographic_method>].

* cited by examiner

SYSTEMS, APPARATUSES, AND METHODS TO MEASURE DEFORMABILITY OF RED BLOOD CELLS IN MICROFLUIDIC CHANNELS

TECHNOLOGICAL FIELD

Example embodiments of the present disclosure relate generally to diagnostic device, and more particularly, to systems, apparatuses, and methods that utilize microfluidic channels and an inline digital holography technique to measure deformability of red blood cells and to determine severity of hematologic disease.

BACKGROUND

Hematologic diseases require early diagnosis and constant monitoring and treatment throughout a patient's lifespan. About 3 million people worldwide suffer from the hematologic disease, like sickle cell disease (SCD), mostly in Africa, India and the Middle East, with an estimated 100,000 affected in the U.S., according to the Centers for Disease Control and Prevention. SCD affects 1 in 375 African American newborns born in the U.S. Early diagnosis through newborn screening, followed by simple interventions, has dramatically reduced SCD related mortality in the US. More than 800 children are born with SCD every day in Africa, and more than half of them die in childhood due to lack of diagnosis and early treatment. Effective treatment of SCD still remains a challenge in preventing childhood and adult mortality, especially in the developing world due to requirements of skilled individuals and the high cost of currently available modalities. Frequent SCD severity monitoring presents insurmountable challenges due to a lack of objective measures of the disease state and the reliance on highly subjective patient-reported symptoms like pain.

The inventors have identified numerous areas of improvement in the existing technologies and processes, which are the subjects of embodiments described herein. Through applied effort, ingenuity, and innovation, many of these deficiencies, challenges, and problems have been solved by developing solutions that are included in embodiments of the present disclosure, some examples of which are described in detail herein.

BRIEF SUMMARY

The following presents a summary of some example embodiments to provide a basic understanding of some aspects of the present disclosure. This summary is not an extensive overview and is intended to neither identify key or critical elements nor delineate the scope of such elements. It will also be appreciated that the scope of the disclosure encompasses many potential embodiments in addition to those here summarized, some of which will be further described in the detailed description that is presented later.

In an example embodiment, a system is disclosed. The system comprises one or more devices having one or more microfluidic channels with at least one cross-sectional dimension smaller than a nominal thickness of a red blood cell. In some embodiments, the one or more devices may correspond to one or more deformability devices. The one or more microfluidic channels with the at least one cross-sectional dimension is configured to deform red blood cells of a blood sample that flow through the one or more microfluidic channels. Further, at least one imager is configured to generate a sequence of digital holography images or videos of the red blood cells of the blood sample that flow through the one or more microfluidic channels. Further, the system includes at least one processor that is operationally coupled to the at least one imager. The at least one processor is configured to receive the sequence of digital holography images or videos; and analyze the generated sequence of digital holography images or videos to quantify and characterize deformability of the red blood cells within the one or more microfluidic channels.

In some embodiments, the one or more microfluidic channels have an interior surface that is coated with a plurality of endothelial cells.

In some embodiments, the one or more microfluidic channels comprises at least one inlet and at least one outlet. The at least one inlet is configured to receive the blood sample and the at least one outlet is configured to discharge the red blood cells.

In some embodiments, to quantify and characterize deformability of the red blood cells within the one or more microfluidic channels, the at least one processor is further configured to measure transit speed or transit times of the red blood cells.

In some embodiments, a speed distribution of the red blood cells of the blood sample is determined based at least on the measured transit speed or transit times of the red blood cells, to indicate a severity of a hematologic disease in the blood sample.

In some embodiments, the speed distribution comprises one or more speed distribution metrics including, but is not limited to, one or more of shape, outliers, average speed, maximum speed, standard deviation, and skewness.

In some embodiments, to quantify and characterize the red blood cells deformed, the at least one processor is further configured to generate a score or relative indicator of a health status or indicate an efficacy of a medical treatment based on the severity of the hematologic disease in the blood sample.

In some embodiments, the at least one imager uses a lensless in-line digital holography configuration to generate the sequence of digital holography images or videos.

In some embodiments, the at least one processor is further configured to analyze the generated sequence of digital holography images or videos using an Artificial Intelligence/Machine Learning module to track the red blood cells within the one or more microfluidic channels.

In some embodiments, the system further comprises at least one user device that is configured to receive a report related to the health status. The red blood cells are unstained, untagged, or unmodified.

In another example embodiment, a method is disclosed. The method comprises steps of: deforming red blood cells of a blood sample flowing through one or more microfluidic channels, wherein the one or more microfluidic channels comprising at least one cross-sectional dimension smaller than a nominal thickness of a red blood cell; generating, via at least one imager, a sequence of digital holography images or videos of the red blood cells of the blood sample flowing through the one or more microfluidic channels; and analyzing, via at least one processor, the generated sequence of digital holography images or videos to quantify and characterize deformability of the red blood cells within the one or more microfluidic channels.

The above summary is provided merely for purposes of summarizing some example embodiments to provide a basic understanding of some aspects of the present disclosure. Accordingly, it will be appreciated that the above-described embodiments are merely examples and should not be construed to narrow the scope or spirit of the present disclosure in any way. It will be appreciated that the scope of the present disclosure encompasses many potential embodiments in addition to those here summarized, some of which will be further described below.

BRIEF DESCRIPTION OF THE DRAWINGS

Figure 1:
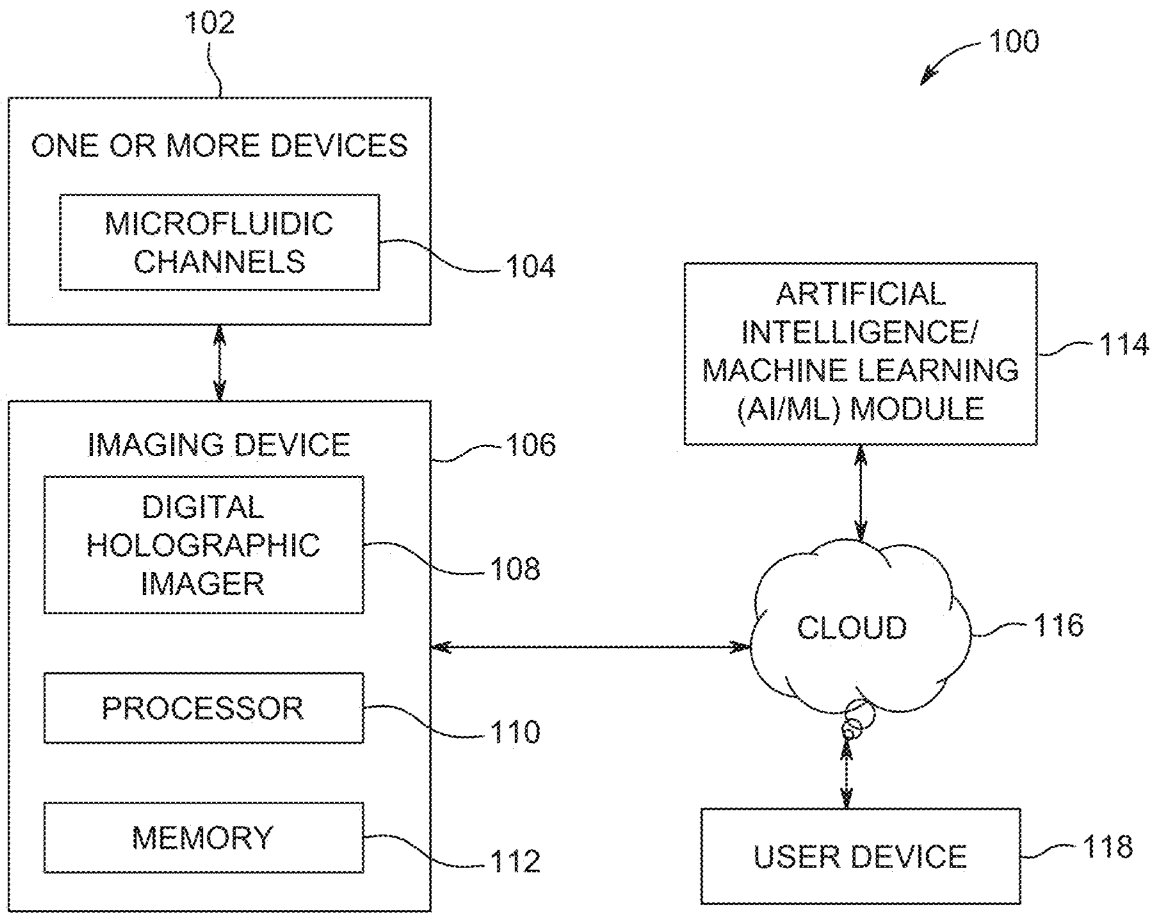
Figure 2A:
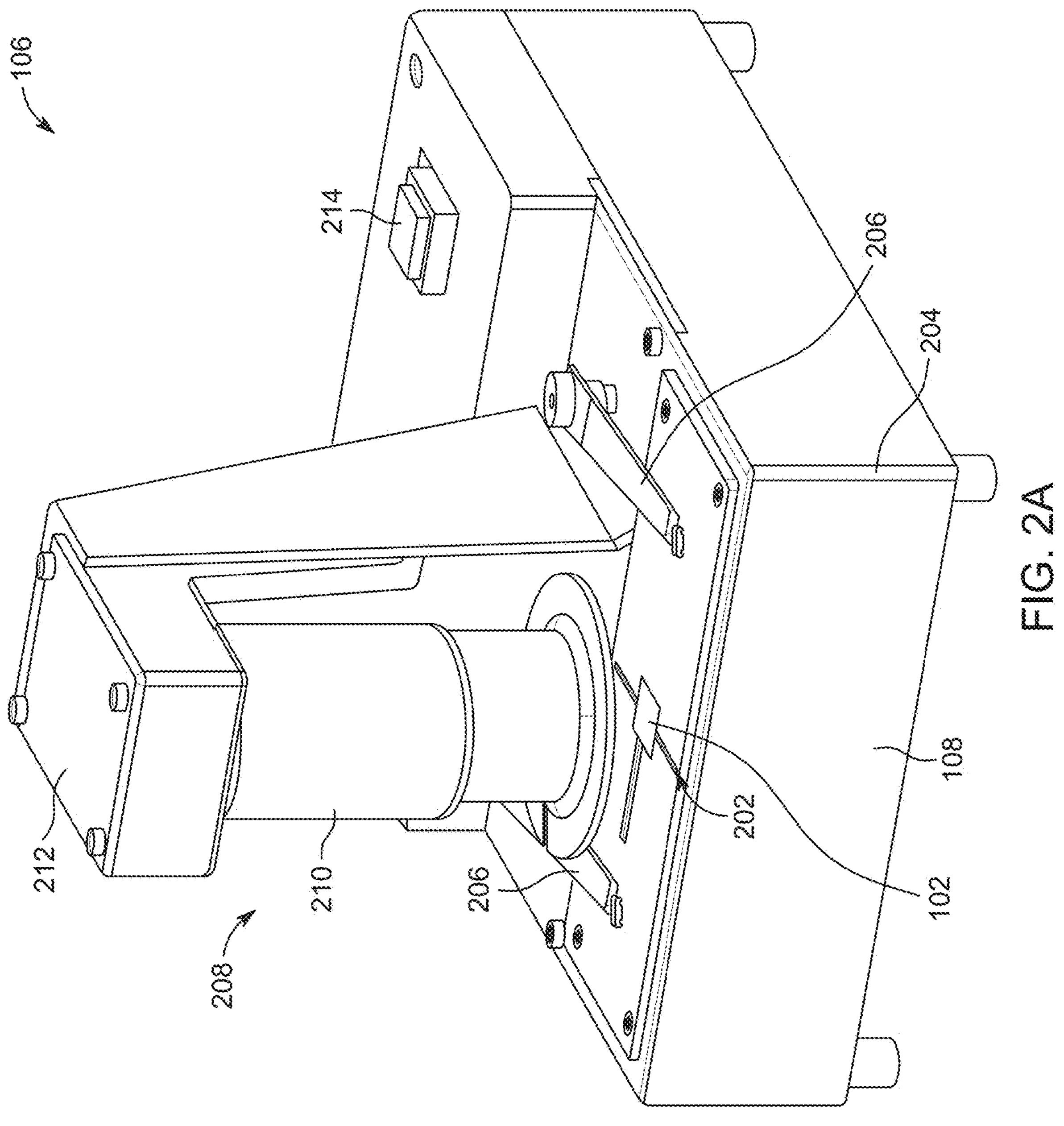
Figure 2B:
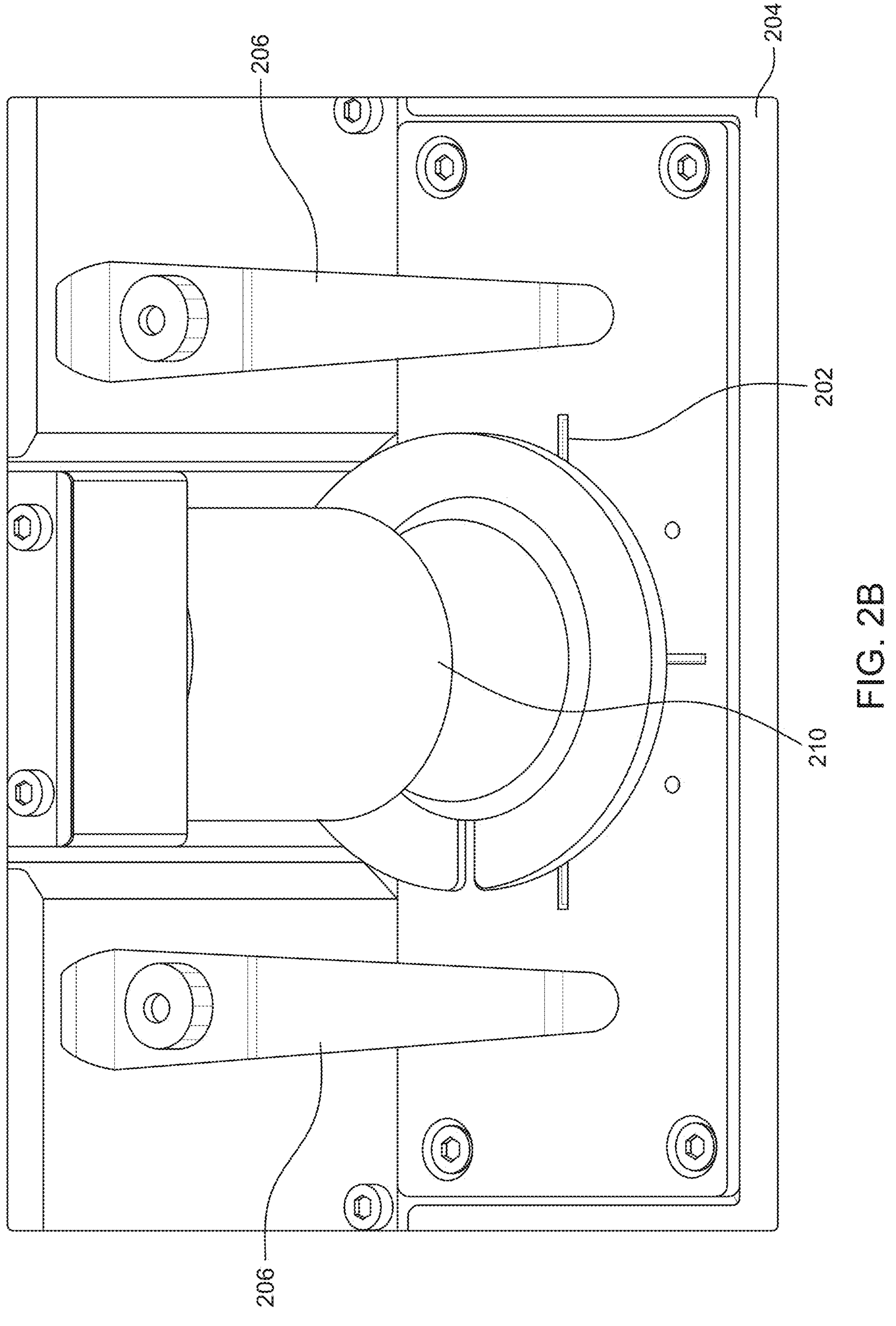
Figure 3:
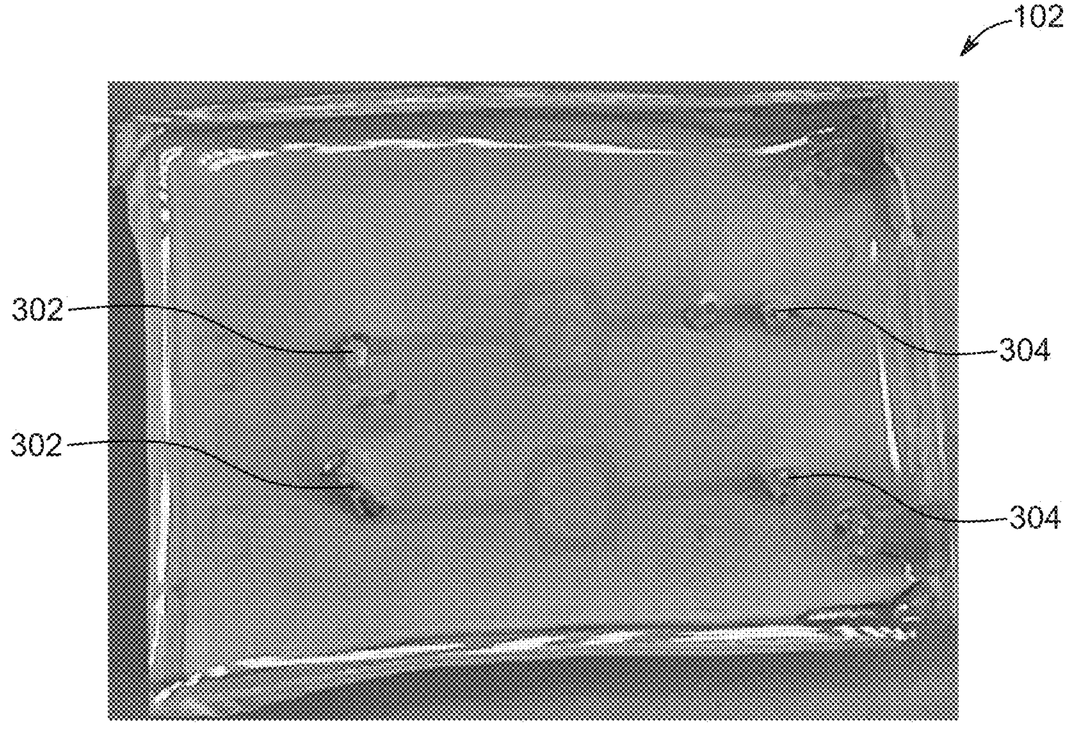
Figure 4A:
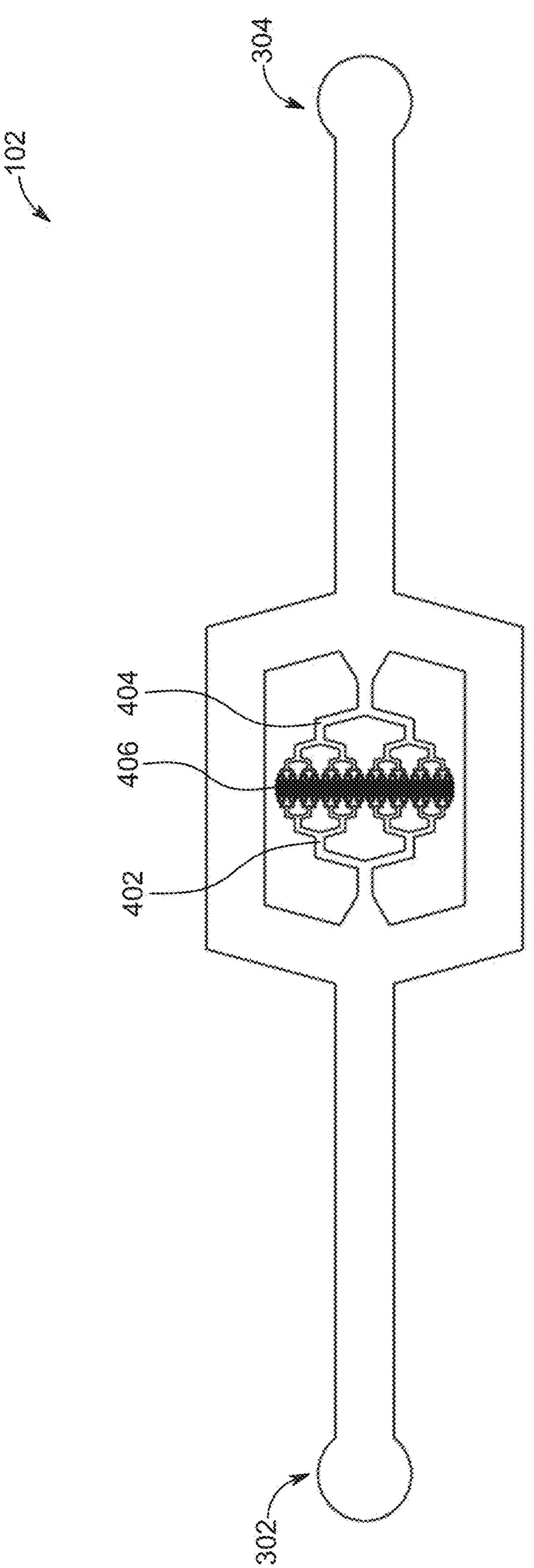
Figure 4B:
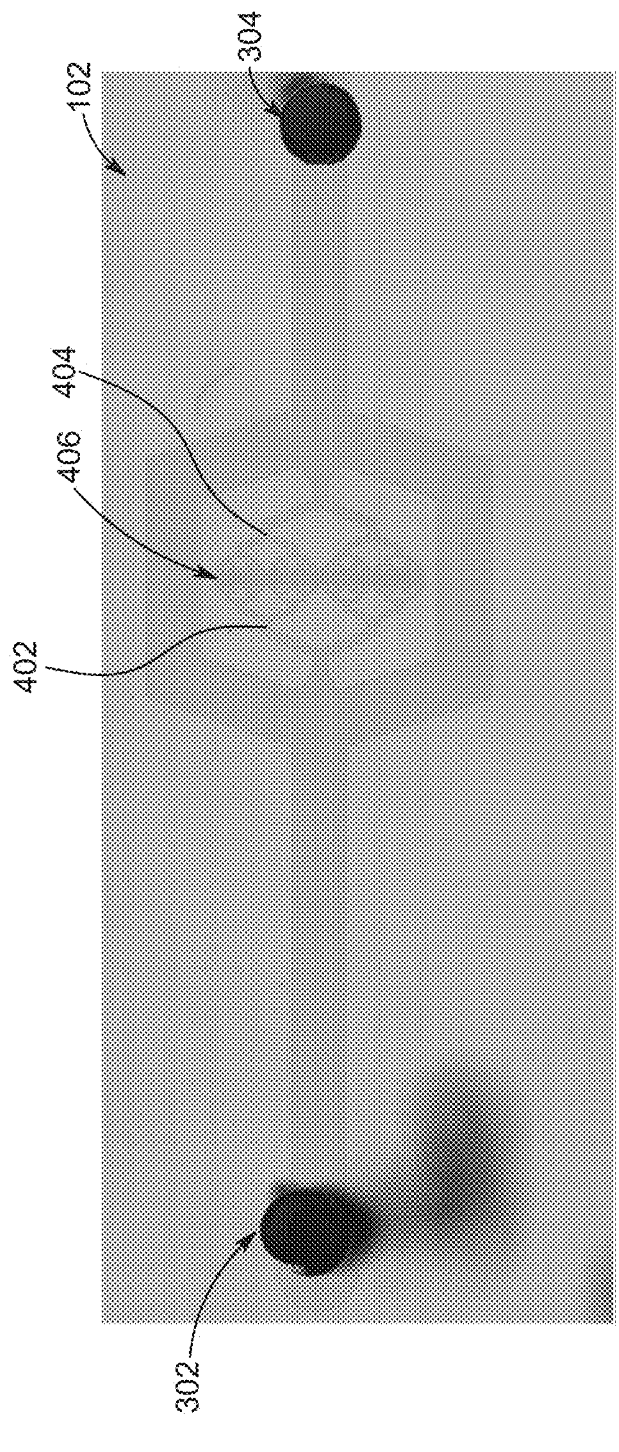
Figure 4C:
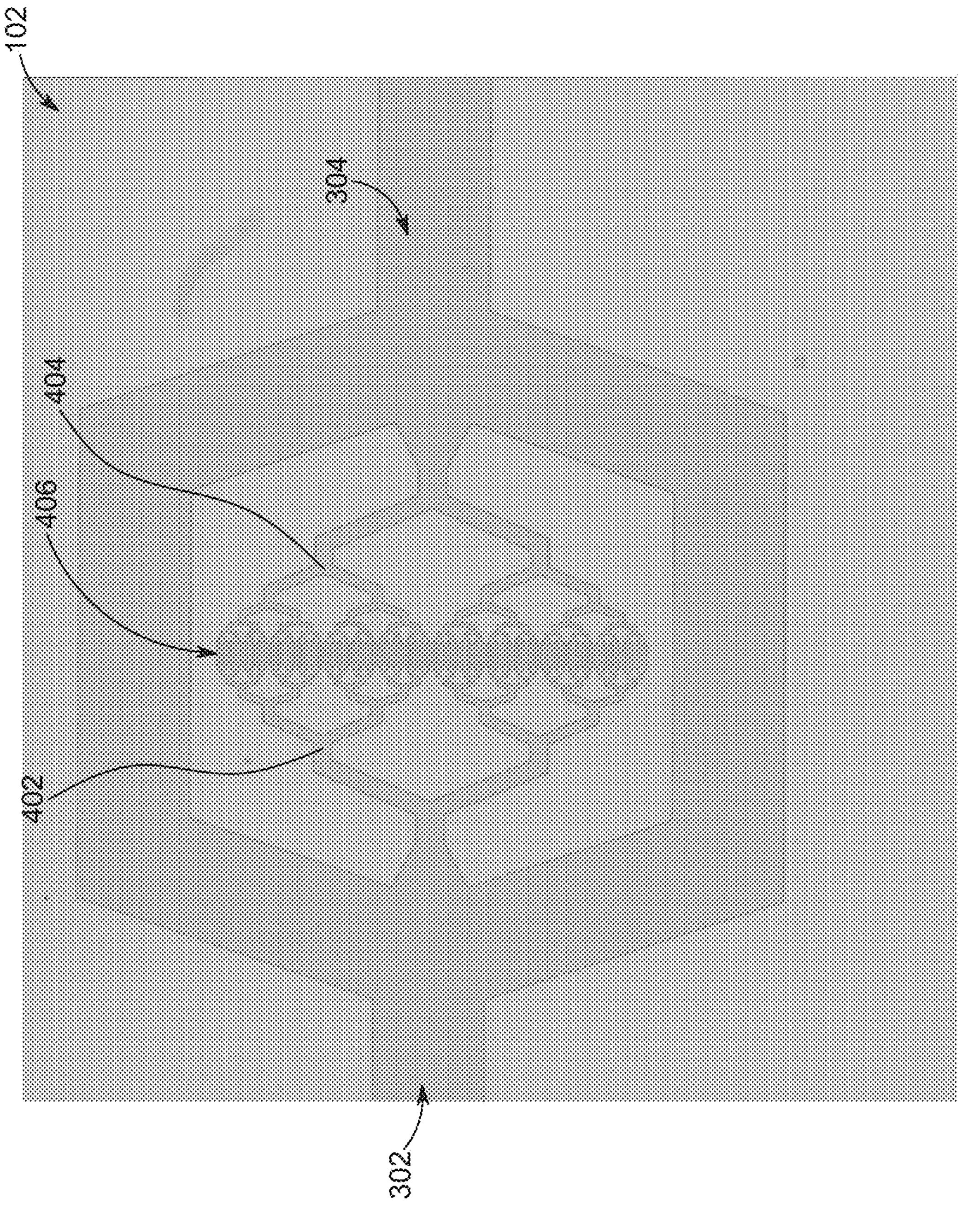
Figure 4D:
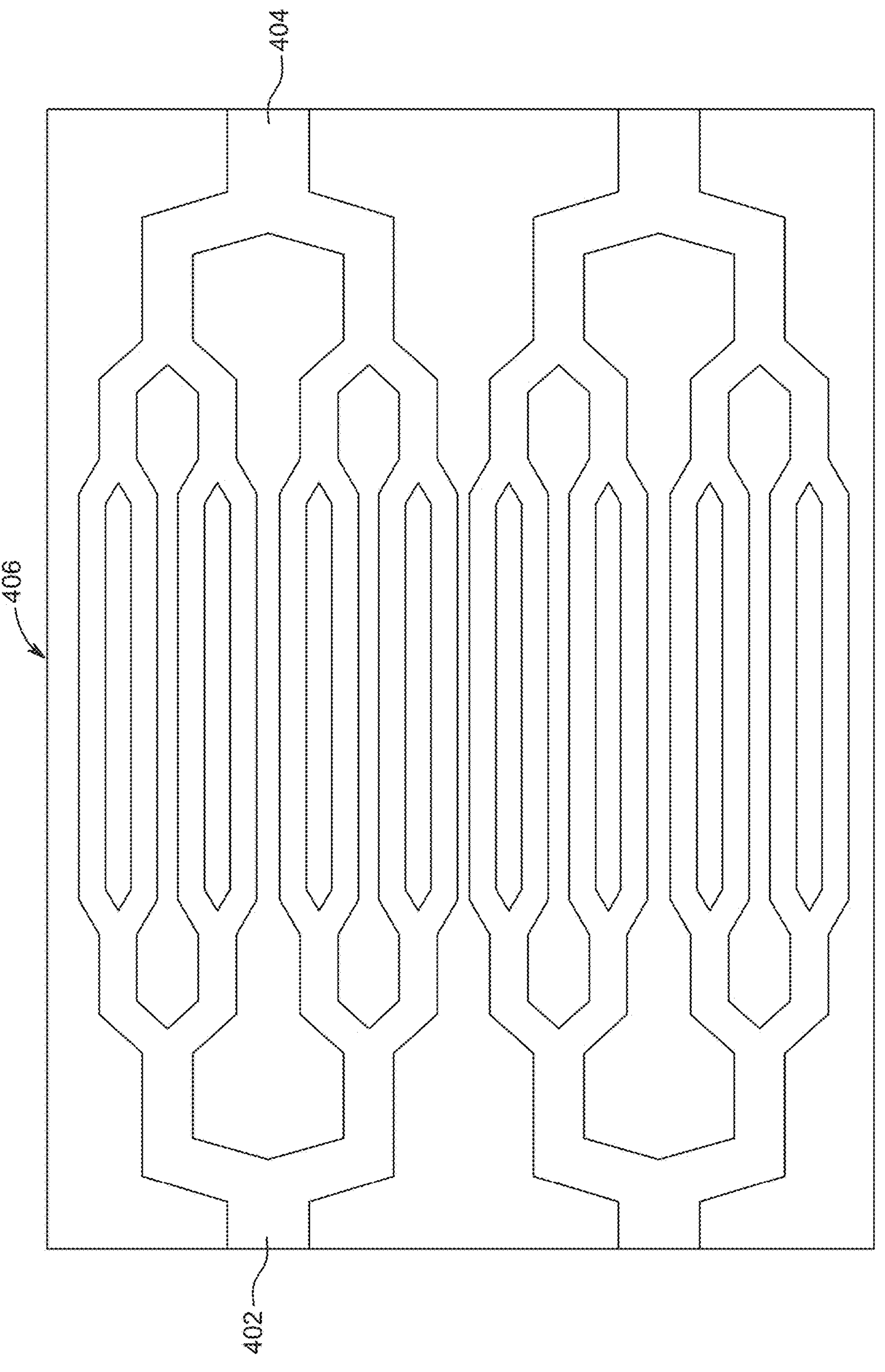
Figure 5:
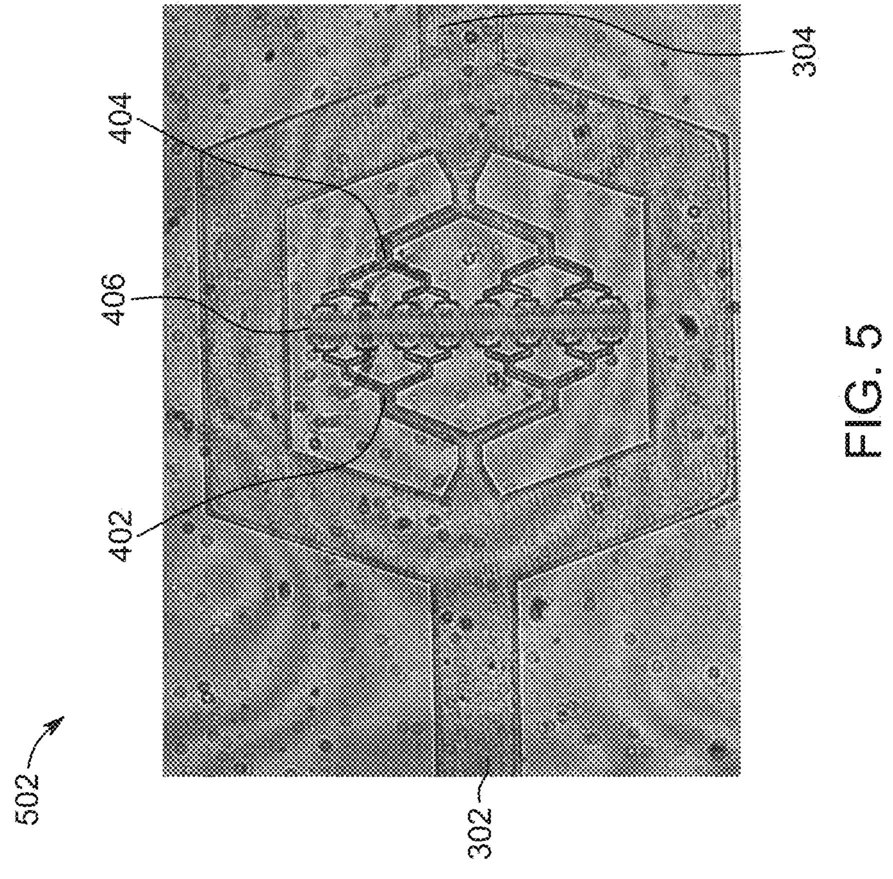
Figure 6:
Figure 6:
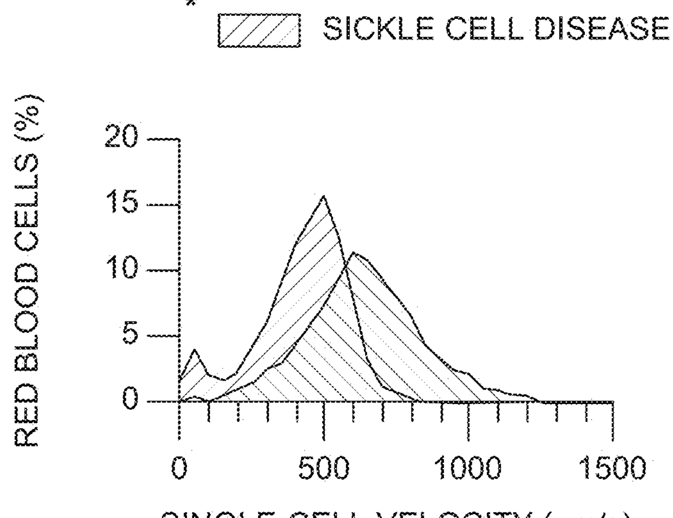
Figure 7A:
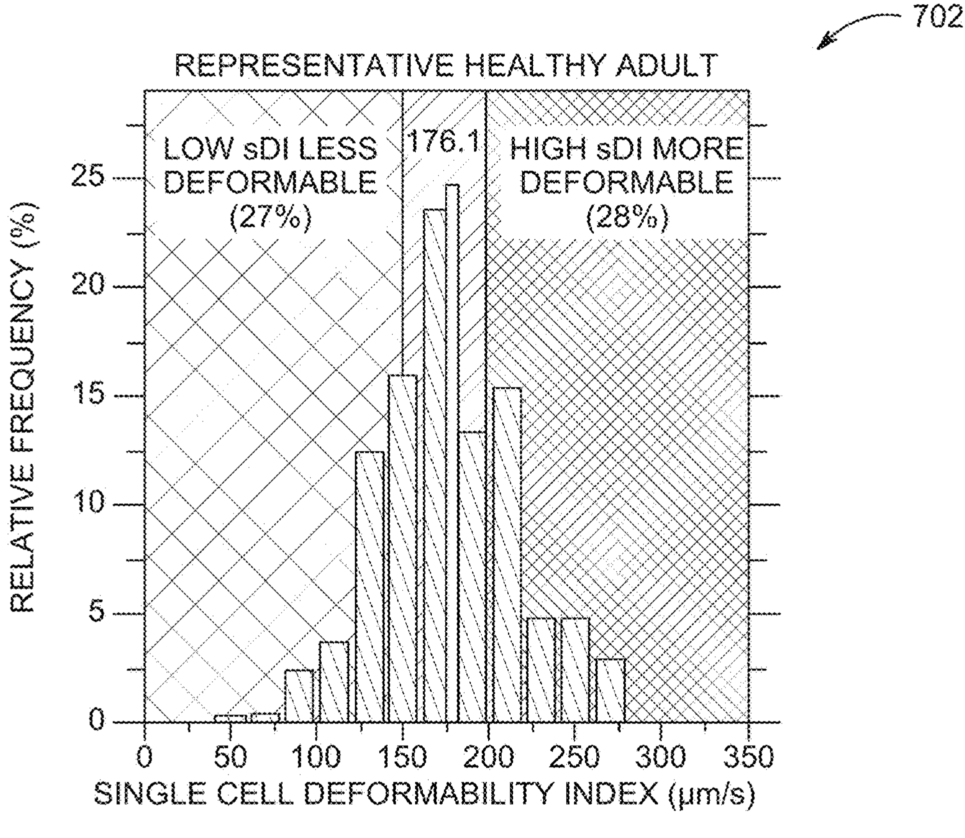
Figure 7B:
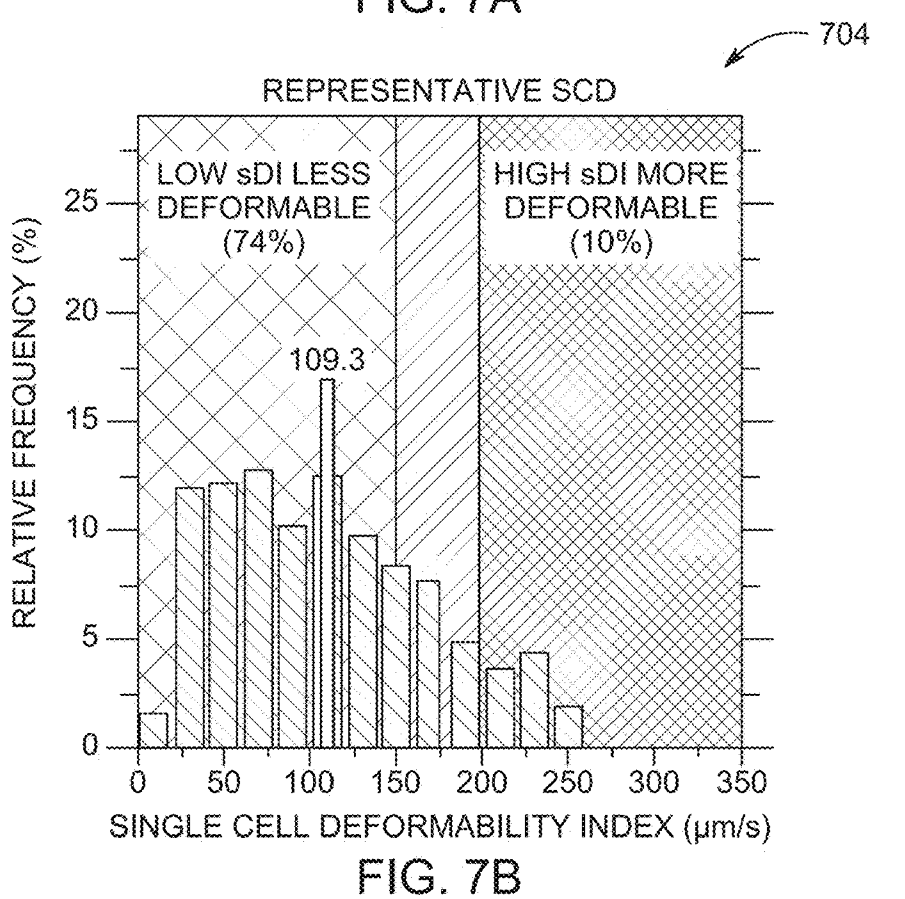
Figures 7C, 7D:
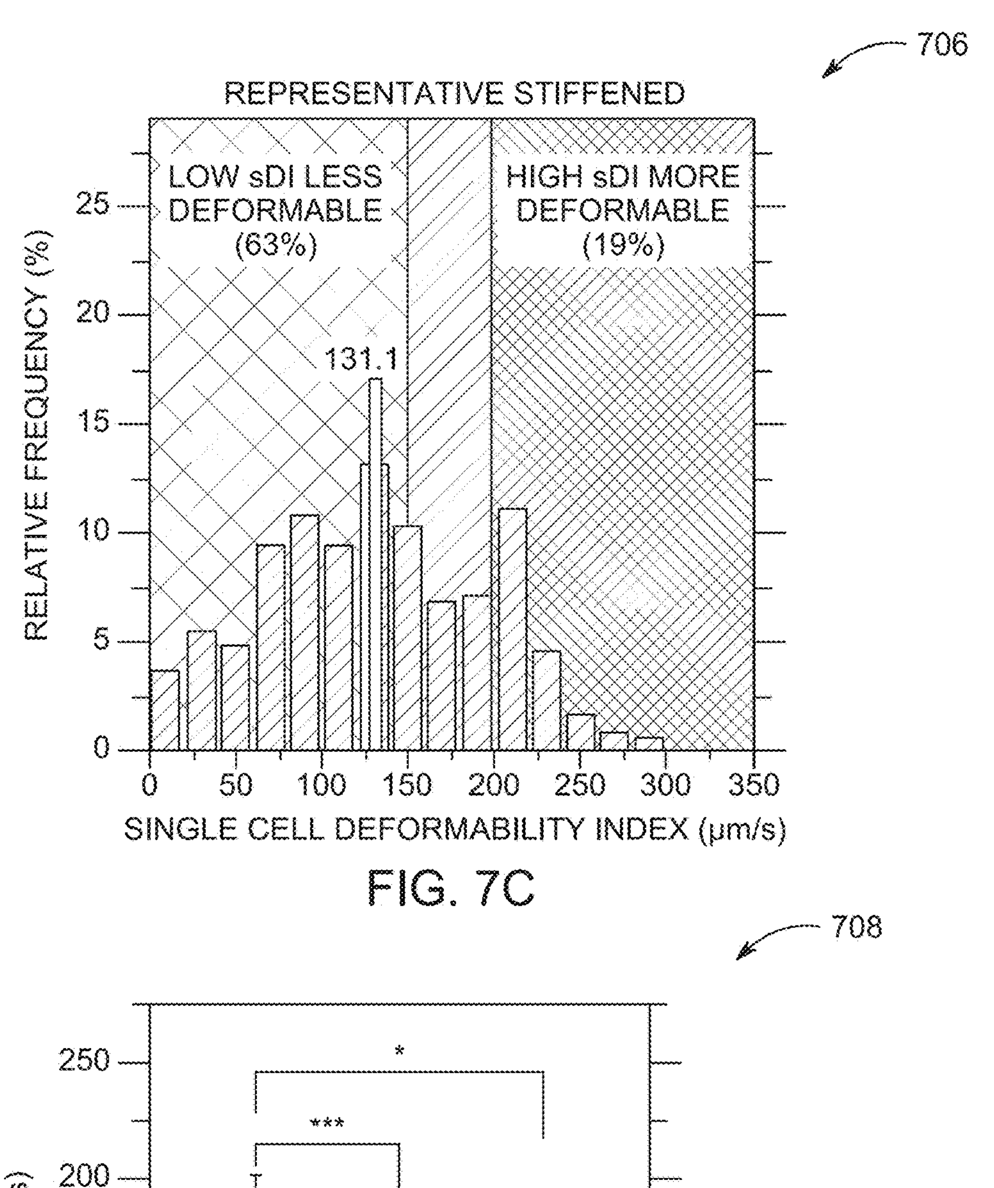
Figure 8:
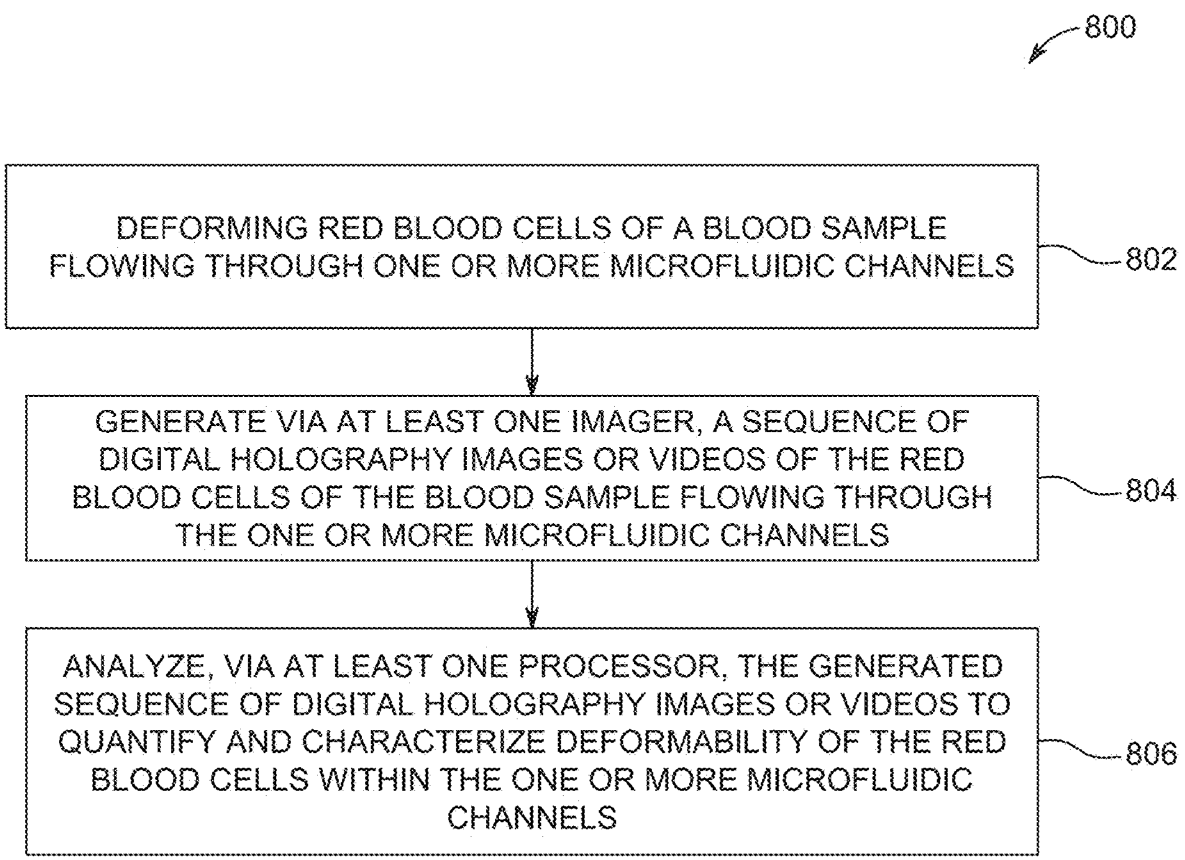
Figure 9:
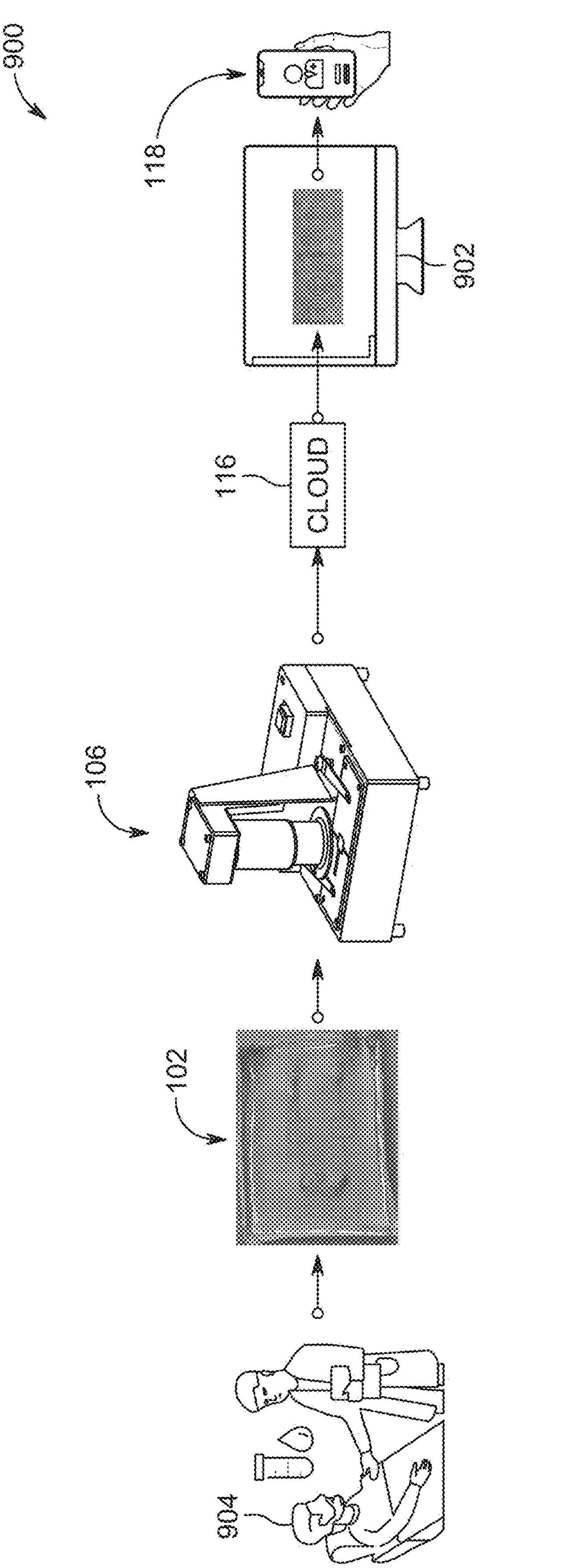

Having thus described certain example embodiments of the present disclosure in general terms, reference will hereinafter be made to the accompanying drawings, which are not necessarily drawn to scale, and wherein:

FIG. 1 illustrates a block diagram of an exemplary system to determine severity of a hematologic disease in accordance with an example embodiment of the present disclosure;

FIG. 2A illustrates a perspective view of an exemplary imaging device in accordance with an example embodiment of the present disclosure;

FIG. 2B illustrates an enlarged view of the exemplary imaging device in accordance with an example embodiment of the present disclosure;

FIG. 3 illustrates an exemplary deformability device with one or more microfluidic channels in accordance with an example embodiment of the present disclosure;

FIG. 4A illustrates the exemplary deformability device with the one or more microfluidic channels having multiple dimensions at various points in accordance with an example embodiment of the present disclosure;

FIG. 4B illustrates an image of another exemplary deformability device with the one or more microfluidic channels in accordance with an example embodiment of the present disclosure;

FIG. 4C illustrates an image of the exemplary deformability device with the one or more microfluidic channels having a branched structure between the at least one inlet and the at least one outlet in accordance with an example embodiment of the present disclosure;

FIG. 4D illustrates an enlarged view of the exemplary deformability device with the one or more microfluidic channels having multiple dimensions at various points in accordance with an example embodiment of the present disclosure;

FIG. 5 illustrates an example of a holographic microscopy image showing dust/debris particles within the one or more microfluidic channels in accordance with an example embodiment of the present disclosure;

FIG. 6 illustrates a graph showing a speed distribution of red blood cells in micrometer per second (μm/s) with respect to a percentage red blood cells in accordance with another example embodiment of the present disclosure;

FIG. 7A illustrates a chart showing single cell deformability index with respect to a percentage relative frequency of a healthy blood sample in accordance with another example embodiment of the present disclosure;

FIG. 7B illustrates another chart showing single cell deformability index with respect to the percentage relative frequency of the SCD blood sample in accordance with another example embodiment of the present disclosure;

FIG. 7C illustrates another chart showing single cell deformability index with respect to the percentage relative frequency of a stiffened blood sample in accordance with another example embodiment of the present disclosure;

FIG. 7D illustrates another chart showing average single cell deformability index of the healthy blood sample, the SCD sample, and the stiffened sample in accordance with another example embodiment of the present disclosure;

FIG. 8 illustrates a flowchart of a method in accordance with an example embodiment of the present disclosure; and FIG. 9 illustrates an exemplary scenario of the system to determine severity of the hematologic disease in accordance with an example embodiment of the present disclosure.

DETAILED DESCRIPTION

Some embodiments will now be described more fully hereinafter with reference to the accompanying drawings, in which some, but not all, embodiments of the present disclosure are shown. Indeed, various embodiments may be embodied in many different forms and should not be construed as limited to the embodiments set forth herein; rather, these embodiments are provided so that this disclosure will satisfy applicable legal requirements.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line for visibility of the underlying components.

As used herein, the term “comprising” means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases “in various embodiments,” “in one embodiment,” “according to one embodiment,” “in some embodiments,” and the like generally mean that the particular feature, structure, or characteristic following the phrase may be included in at least one embodiment of the present disclosure and may be included in more than one embodiment of the present disclosure (importantly, such phrases do not necessarily refer to the same embodiment).

The word “example” or “exemplary” is used herein to mean “serving as an example, instance, or illustration.” Any implementation described herein as “exemplary” is not necessarily to be construed as preferred or advantageous over other implementations.

If the specification states a component or feature “may,” “can,” “could,” “should,” “would,” “preferably,” “possibly,” “typically,” “optionally,” “for example,” “often,” or “might” (or other such language) be included or have a characteristic, that a specific component or feature is not required to be included or to have the characteristic. Such a component or feature may be optionally included in some embodiments or it may be excluded.

The present disclosure provides various embodiments of systems and methods to measure deformability of red blood cells in microfluidic channels. Embodiments may allow red blood cells of a blood sample to flow through the microfluidic channels having at least one cross-sectional dimension smaller than a nominal thickness of a red blood cell. Embodiments may generate sequence of digital holography images or videos of the red blood cells transiting through the microfluidic channels. Embodiments may analyze the generated sequence of digital holography images or videos to quantify and characterize deformability of the red blood cells passing through the one or more microfluidic channels. Thereafter, a report related to user's health status is generated to show severity of a hematologic disease i.e., sickle cell disease (SCD) in the red blood cells.

FIG. 1 illustrates a block diagram of a system 100 to determine severity of a hematologic disease, in accordance with an example embodiment of the present disclosure.

The system 100 may comprise one or more devices 102 having one or more microfluidic channels 104, and at least one imaging device 106. In some embodiments, the one or more devices 102 may correspond to one or more deformability devices 102. Further, the at least one imaging device 106 may comprise at least one imager 108 and at least one processor 110 operated on some stored instructions in a memory 112. The one or more microfluidic channels 104 may have at least one cross-sectional dimension. The at least one cross-sectional dimension of the one or more microfluidic channels 104 may be smaller than a nominal thickness of a red blood cell such that each red blood cell from a blood sample deforms in order to pass through the one or more microfluidic channels 104. In some embodiments, the one or more microfluidic channels 104 may have an interior surface that is coated with a plurality of endothelial cells. It may be noted that a single cell layer of the plurality of endothelial cells may line all blood vessels and regulate exchanges between bloodstream and surrounding tissues. In some other embodiments, the interior surface of the one or more microfluidic channels 104 may be coated using Laminin or p-selectin. In some example embodiments, various other coating options may exist depending on which pharma medication is being evaluated for efficacy, without departing from the scope of the disclosure.

In some embodiments, the at least one imager 108 may be configured to generate a sequence of digital holography images or videos of the blood sample transiting through the one or more microfluidic channels 104. The at least one imager 108 may be referred to as a digital holographic imager. In some embodiments, the at least one imager 108 may use a lensless in-line digital holography configuration to generate the sequence of digital holography images or videos. In some embodiments, the at least one processor 110 may utilize angular spectrum propagation for modelling the propagation of a wave field to generate the sequence of reconstructed digital holography images or videos.

The at least one processor 110 may be operationally coupled to the at least one imager 108. The at least one processor 110 may be configured to receive the sequence of digital holography images or videos. The at least one processor 110 may be configured to analyze the generated sequence of digital holography images or videos to determine severity of the hematologic disease. In some embodiments, the hematologic disease may correspond to diseases relating to red blood cells or hemoglobin, such as white blood cells, leukocytes, Platelets etc. In some embodiments, the hematologic disease may correspond to sickle cell disease. The detailed working of the at least one processor 110 may be described in greater detail in FIGS. 2A-4D.

In some embodiments, the at least one processor 110 may include suitable logic, circuitry, and/or interfaces that are operable to execute one or more instructions stored in the memory 112 to perform predetermined operations. In one embodiment, the at least one processor 110 may be configured to decode and execute any instructions received from one or more other electronic devices or server(s). The at least one processor 110 may be configured to execute one or more computer-readable program instructions, such as program instructions to carry out any of the functions described in this description. Further, the processor may be implemented using one or more processor technologies known in the art. Examples of the processor include, but are not limited to, one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor).

Further, the memory 112 may be communicatively coupled to the at least one processor 110. In some embodiments, the memory 112 may be configured to store a set of instructions and data executed by the at least one processor 110. Further, the memory 112 may include the one or more instructions that are executable by the at least one processor 110 to perform specific operations. It is apparent to one skilled in the art that one or more instructions stored in the memory 112 enable the hardware of the system 100 to perform the predetermined operations. Some of the commonly known memory implementations include, but are not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

Further, the system 100 may comprise an Artificial Intelligence/Machine Learning (AI/ML) module 114 communicatively coupled to the at least one processor 110 via a cloud 116. The at least one processor 110 along with the AI/ML module 114 may analyze the generated sequence of digital holography images or videos to quantify and characterize deformability of the red blood cells within the one or more microfluidic channels 104. Such quantification of the deformations of the red blood cells formed within the one or more microfluidic channels 104 may be configured to generate a score or relative indicator of a user's health status or indicate an efficacy of a medical treatment of the user based on a severity of the hematologic disease in the red blood cells. In some embodiments, the AI/ML module 114 may be configured to detect and classify each cell. The classification may be to ensure that the detected cells are the red blood cells and not some other cell type or dust/debris. In some alternate embodiments, the AI/ML module 114 may be integrated within the at least one imager 108 to analyze the generated sequence of digital holography images or videos without the need for remotely monitoring via the cloud 116. The AI/ML module 114 may segregate the red blood cells from other elements present in the image, without departing from the scope of the disclosure.

In some embodiments, the cloud 116 may facilitate a communication link between the AI/ML module 114 and the at least one processor 110. The cloud 116 may be referred as a network interface that facilitates a communication link among the other components of the system 100. Further, the cloud 116 may be a wireless network and/or a wired network. The cloud 116 may be implemented using one or more communication techniques. The one or more communication techniques may be Radio waves, Wi-Fi, Bluetooth, ZigBee, Z-wave and other communication techniques, known in the art.

The system 100 may further include at least one user device 118 that is configured to receive the quantified deformability of the red blood cells to display a report related to the user's health status. The at least one user device 118 may be wired to the at least one processor 110 or may be coupled via the cloud 116. In some embodiments, the at least one user device 118 may be separate and remote from the system 100 and the system 100 may communicate with the remote user device 100. In some embodiments, the at least one user device 118 may be wired to the at least one processor 110 or may be coupled, via the cloud 116. In some embodiments, the at least one user device 118 may include a wired or wireless devices operationally coupled to the system 100. For example, a desktop or laptop computer, any tablet, smart phone, or other handheld devices.

Further, the system 100 may include an input/output circuitry (not shown) that may enable a user to communicate or interface with the system 100 via the at least one user device 118. In some example embodiments, the at least one user device 118 may include a control room computer system or other portable electronic devices. The input/output circuitry may act as a medium transmit input from the at least one user device 118 to and from the system 100. In some embodiments, the input/output circuitry may refer to the hardware and software components that facilitate the exchange of information between the user and the system 100. In one example, the system 100 may include a graphical user interface (GUI) (not shown) as input circuitry to allow the user to input data via the at least one user device 118. The input/output circuitry may include various input devices such as keyboards, barcode scanners, GUI for the user to provide data and various output devices such as displays, printers for the user to receive data. In another example, the input/output circuitry may include various output circuitry such as indicators to indicate the correct and incorrect placement of the device 102.

In some alternate embodiments, the system 100 may include a communication circuitry (not shown). The communication circuitry may allow the at least one imaging device 106 and the at least one user device 118 to exchange data or information with other systems. Further, the communication circuitry may include network interfaces, protocols, and software modules responsible for sending and receiving data or information. In some embodiments, the communication circuitry may include Ethernet ports, Wi-Fi adapters, or communication protocols like HTTP or MQTT for connecting with other systems. The communication circuitry may allow the system 100 to stay up-to-date and accurately track levels of deformation of blood sample/cells deformed within the one or more microfluidic channels 104.

It will be apparent to one skilled in the art the above-mentioned components of the system 100 have been provided only for illustration purposes. In some embodiments, the system 100 may include other components as well, without departing from the scope of the disclosure.

FIG. 2A illustrates a perspective view of the at least one imaging device 106, in accordance with an example embodiment of the present disclosure. FIG. 2B illustrates an enlarged view of the at least one imaging device 106, in accordance with an example embodiment of the present disclosure. FIGS. 2A-2B are described in conjunction with FIG. 1.

The at least one imaging device 106 may comprise a cross hair 202 positioned above a housing 204. In some embodiments, the device 102 having the one or more microfluidic channels 104 may be placed on the cross hair 202 of the housing 204. The one or more microfluidic channels 104 may be positioned firmly on the cross hair 202 using one or more clamps 206. The one or more clamps 206 may correspond to metal plates that may be rotatably fixed at one end and free at other end. The free end may be slide onto the one or more microfluidic channels 104 once placed over the housing 204. The one or more microfluidic channels 104 placed on the cross hair 202 may be caused to pass an individual red blood cell of the blood sample through the one or more microfluidic channels 104. The individual red blood cell may be deformed within the one or more microfluidic channels 104. The one or more microfluidic channels 104 may be placed at any other position of the housing 204 as well, without departing from the scope of the disclosure.

As discussed above, the imaging device 106 may comprise at least one imager 108 and at least one processor 110. Further, the at least one imager 108 may be configured to generate sequence of digital holography images or videos (not shown) of the red blood cells of the blood sample transiting through the one or more microfluidic channels 104. Further, the at least one imager 108 may be referred to as a digital holographic imager. In some embodiments, the at least one imager 108 may use a lensless in-line digital holography configuration to generate the sequence of the digital holography images or videos.

The at least one imaging device 106 may comprise an illumination source 208 that may be directed towards the one or more microfluidic channels 104. In various embodiments, the at least one imaging device 106 may be vertically directed towards the one or more microfluidic channels 104. The illumination source 208 may be configured to facilitate the at least one imager 108 to generate the sequence of digital holography images or videos. In some embodiments, the illumination source 208 may comprise a height adjustable light tube 210 and a laser driver 212 that may be installed above the at least one imager 108. The height adjustable light tube 210 may be a telescopic structure with adjustment of height from the one or more microfluidic channels 104 placed on the cross hair 202 of the housing 204. Further, the at least one imaging device 106 may be provided with a switch 214 to control the laser driver 212 and thereby the illumination source 208. In some embodiments, the illumination source 208 may be positioned at a height, e.g., 8 centimeters (cm) from the device 102, such that red blood cells of the blood sample inside the one or more microfluidic channels 104 may receive a uniform laser beam.

Further, the at least one processor 110 may be communicatively coupled to the at least one imager 108. The at least one processor 110 may be configured to receive the sequence of digital holography images or videos. Further, the at least one processor 110 may analyze the generated sequence of digital holography images or videos to quantify and characterize deformability of the red blood cells formed within the one or more microfluidic channels 104. In some embodiments, the deformability of the red blood cells is quantified to generate a score or relative indicator of a user's health status and indicate the efficacy of a medical treatment of the user based on the severity of the hematologic disease. The user may refer to a patient having a medical condition. Alternatively, a user may be a medical professional, such as a doctor. In one example embodiment, the score or relative indicator may include one or more reference ranges to allow for quick indication of the severity of the hematologic disease. In some embodiments, the score may include one or more reference ranges to allow for quick indication of the severity of a sickle cell disease (SCD).

In some embodiments, the at least one processor 110 may be configured to analyze the generated sequence of digital holography images or videos using the AI/ML module 114. In some embodiments, the generated sequence of digital holography images or videos may be analyzed to provide a distribution of the deformability of the red blood cells within a blood sample.

FIG. 3 illustrates the device 102 with the one or more microfluidic channels 104, in accordance with an example embodiment of the present disclosure. FIG. 3 is described in conjunction with FIGS. 1, 2A, and 2B.

The device 102 may comprise at least one deformability device inlet 302 and at least one deformability device outlet 304. In some embodiments, the at least one deformability device inlet 302 may receive the blood sample and the at least one deformability device outlet 304 may allow to discharge the deformed red blood cells through the one or more microfluidic channels 104. In various embodiments, the at least one deformability device inlet 302 and the at least one deformability device outlet 304 may correspond to deformation device inlet and deformation device outlet respectively. Further, the blood sample may flow towards the at least one deformability device outlet 304 of the device 102 via the one or more microfluidic channels 104. It will be apparent that dimensions of the at least one deformability device inlet 302 and the at least one deformability device outlet 304 of the device 102 may be same. The one or more microfluidic channels 104 may be described in conjunction with FIGS. 4A-4D.

FIG. 4A illustrates the device 102 with the one or more microfluidic channels 104 having multiple dimensions at various points, in accordance with an example embodiment of the present disclosure. FIG. 4B illustrates another exemplary device 102 with the one or more microfluidic channels 104 having at least one inlet 402 and at least one outlet 404 in accordance with an example embodiment of the present disclosure. FIG. 4C illustrates an enlarged view of the exemplary device 102 with the one or more microfluidic channels 104 having a branched structure 406 between the at least one inlet 402 and the at least one outlet 404 in accordance with an example embodiment of the present disclosure. FIG. 4D illustrates an enlarged view of the device 102 with the one or more microfluidic channels 104 having multiple dimensions at various points, in accordance with an example embodiment of the present disclosure. FIGS. 4A-4D are described in conjunction with FIGS. 1, 2A-2B, and 3.

As illustrated in FIG. 4A, the one or more microfluidic channels 104 may have the branched structure 406, between the at least one inlet 402 and the at least one outlet 404. In various embodiments, the at least one inlet 402 and the at least one outlet 404 may correspond to a microfluidic channel inlet and microfluidic channel outlet respectively. The one or more microfluidic channels 104 have a predefined cross-sectional area at the various points between the at least one inlet 402, the branched structure 406 and the at least one outlet 404. The blood sample, after flowing from the at least one deformability device inlet 302, may pass from the at least one inlet 402 to the at least one outlet 404 via the branched structure 406. The branched structure 406 may have small cross-section compared to the at least one inlet 402. The branched structure 406 may have dimension smaller than a nominal thickness of a red blood cell. The branched structure 406 may allow deformation of red blood cells of the blood sample flowing from the at least one inlet 402 and the at least one outlet 404 of the one or more microfluidic channels 104. It will be apparent that the dimensions of the at least one inlet 402 and the at least one outlet 404 may be greater than the dimensions of the branched structure 406. In various embodiments, the diseased cell may not deform to pass through the branched structure 406.

In some embodiments, the interior surface of the one or more microfluidic channels 104 may be coated with a plurality of endothelial cells. In some example embodiments, various other coating options may exist depending on which pharma medication is being evaluated for efficacy. For example, a healthy cell may be deformed and may flow between the at least one inlet 402 via the branched structure 406 towards the at least one outlet 404 in a suitable time frame without getting clogged within the interior surface of the one or more microfluidic channels 104. The suitable time frame may include a few seconds or few milli-seconds depending upon flow speed of the blood sample.

As illustrated in FIGS. 4B-4C, the branched structure 406 of the one or more microfluidic channels 104 may facilitate flow of the red blood cells. For example, an individual red blood cell may be deformed to transit through the branched structure 406 to flow towards the at least one outlet 404 of the one or more microfluidic channels 406 and then towards the at least one deformability device outlet 304 of the device 102. A healthy red blood cell may deform easily in order to transit through one of the channels within the branched structure 406. A diseased red blood cell, i.e., SCD red blood cell, may resist deforming while transiting through the branched structure 406 and therefore transit at a relatively lower speed.

As illustrated in FIG. 4D, the one or more microfluidic channels 104 may have multiple dimensions at the various points. The various points may include at least one inlet 402, the at least one outlet 404 and the branched structure 406. In some embodiments, the one or more microfluidic channels 104 may have dimensions of width and length of 6 um*90 um at the branched structure 406, 8 um*20 um proximal to the at least one inlet 402 and the at least one outlet 404, and 12 um*28 um at the at least one inlet 402 and the at least one outlet 404.

FIG. 5 illustrates an example of a holographic microscopy image 502 showing dust/debris particle within the one or more microfluidic channels 104 at various points, in accordance with an example embodiment of the present disclosure. FIG. 5 is described in conjunction with FIGS. 1-4D.

As illustrated in FIG. 5, the holographic microscopy image 502 of the one or more microfluidic channels 104 may classify the dust particles present within the one or more microfluidic channels 104 between the at least one inlet 402 and the at least one outlet 404. It may be noted that the red blood cells may easily flow between the at least one inlet 402 towards the at least one outlet 404 via the branched structure 406 of the one or more microfluidic channels 104. The blood sample, i.e., the red blood cells in the normal blood sample may deform within the branched structure 406. Also, a diseased red blood cell flowing from the at least one inlet 402 may not easily deform within the branched structure 406. As discussed above, the sequence of digital holography images captured by the at least one imager may confirm deformability of the blood sample within the branched structure 406 of the one or more microfluidic channels 104.

The holographic microscopy image 502 may be generated by the at least one imager 108. Further, the holographic microscopy image 502 may be analyzed by the sequence of digital holography images or videos of the suitable time frame. In one example, the at least one imager 108 may capture a video of 60 seconds showing flow of red blood cells from the at least one inlet 402 towards the at least one outlet 404. It will be apparent that the flow of the blood sample between the at least one inlet 402 towards the at least one outlet 404 varies according to the severity of the blood sample. The diseased red blood cells may not easily be deformed within the branched structure 406, while the healthy blood cells may easily deform and pass easily towards the at least one outlet 404.

As discussed, the at least one processor 110 may be configured to analyze the generated sequence of digital holography images or videos using the AI/ML module 114 to detect transit speed and transit time of red blood cells transiting the microfluidic channels 104. Further, the quantification and characterization of the deformability of red blood cells within the one or more microfluidic channels 104 may be configured to generate a score or relative indicator of a health status and/or indicate an efficacy of a medical treatment of the user based on the severity of a hematologic disease in the blood sample.

FIG. 6 illustrates a graph 600 showing a bi-modal distribution of a speed of red blood cells in a sickle cell disease sample in micrometer per second (um/s) with respect to a percentage red blood cells in accordance with another example embodiment of the present disclosure. FIG. 6 is described in conjunction with FIGS. 1-5.

The deformability of the red blood cells may be characterized by the speed distribution of red blood cells flowing within the one or more microfluidic channels 104. In some embodiments, the diseased blood sample may exhibit slower speed distributions compared to healthy i.e., normal blood samples. Therefore, single-cell speed of the diseased red blood cells may be smaller than the single-cell speed of the healthy red blood cells.

As illustrated in FIG. 6, for a given blood sample, total number of deformed red blood cells, i.e., healthy cells may vary according to variations in the percentage of the red blood cells and the flow speed within the one or more microfluidic channels 104. In some example embodiments, the amount of red blood cells in the given blood sample may vary between 2% to 20% with respect to the single-cell speed of between 0 to 1500 um/s. In some embodiments, the speed distribution of healthy cells at a given point within the one or more microfluidic channels 104 may be faster compared to the speed distribution of the diseased red blood cells (SCD) at that given point within the one or more microfluidic channels 104. It may be noted that the diseased red blood cells may show a smaller fraction in faster speeds of the speed distribution.

FIG. 7A illustrates a chart 702 showing single cell deformability index with respect to a percentage relative frequency of a healthy blood sample, in accordance with another example embodiment of the present disclosure. FIG. 7B illustrates another chart 704 showing single cell deformability index with respect to the percentage relative frequency of the SCD blood sample, in accordance with another example embodiment of the present disclosure. FIG. 7C illustrates another chart 706 showing single cell deformability index with respect to the percentage relative frequency of a stiffened blood sample, in accordance with another example embodiment of the present disclosure. FIG. 7D illustrates another chart 708 showing average single cell deformability index of the healthy blood sample, the SCD sample, and the stiffened sample, in accordance with another example embodiment of the present disclosure.

As illustrated in FIG. 7A, the chart 702 indicates the single-cell speed distribution of an adult blood sample by evaluating a single cell deformability index (sDI). The sDI may be an indicator of the red blood cells between the healthy cells and the diseased cells. A higher sDI may indicate that the red blood cells are more deformable, i.e., healthy, and a lower sDI may indicate that the red blood cells are less deformable i.e., diseased cells or SCD. In some example embodiments, a low sDI range may indicate that the red blood cells in the blood sample may undergo less deformation, e.g., 27% of the blood sample. In some other example embodiments, a high sDI range may indicate that the red blood cells in the blood sample may undergo more deformation, e.g., 28% of the blood sample. The average sDI of the healthy blood sample may be around 176.1 μm/s. In some other example embodiments, the red blood cells in the adult blood sample may have 45% deformation in a range between the high sDI range and the low sDI range.

As illustrated in FIG. 7B, the chart 704 indicates the single-cell speed distribution of the SCD blood sample by evaluating the sDI. The chart 704 indicates that the SCD blood sample may have 74% of the red blood cells in the low sDI range and 10% of the red blood cells in the high sDI range. The average sDI of the SCD blood sample may be around 109.3 μm/s.

As illustrated in FIG. 7C, the chart 706 indicates the single-cell speed distribution of the stiffened blood sample. The chart 706 indicates that the stiffened blood sample may have 63% of the red blood cells in the low sDI range and only 19% of the red blood cells in the high sDI range. The average sDI of the stiffened blood sample may be around 131.1 μm/s.

As illustrated in FIG. 7D, the chart 708 indicates average sDI of the healthy blood sample, the SCD sample, and the stiffened sample. As discussed above, for a given quantity of red blood samples, i.e., n=6, the sDI range of the healthy blood sample may be averaged to 176.1 μm/s, the sDI range of the SCD sample may be averaged to 109.3 μm/s and the sDI range of the stiffened blood sample may be averaged to 131.1 μm/s.

FIG. 8 illustrates a flowchart of a method of determining severity of the hematologic disease i.e., sickle cell disease, in accordance with an example embodiment of the present disclosure. FIG. 8 is described in conjunction with FIGS. 1-7D.

At operation 802, the red blood cells of the blood sample may be deformed by flowing through the one or more microfluidic channels 104. As discussed above, the branched structure 406 may have at least one cross-sectional dimension smaller than a nominal thickness of a red blood cell.

At operation 804, the sequence of digital holography images or videos of the red blood cells of the blood sample flowing through the one or more microfluidic channels 104 may be generated by the at least one imager 108. In some embodiments, the at least one imager 108 may use a lensless in-line digital holography configuration to generate the sequence of digital holography images or videos.

At operation 806, the generated sequence of digital holography images or videos may be analyzed to quantify and characterize deformability of the red blood cells within the one or more microfluidic channels 104. In some embodiments, the quantification and characterization of the deformability of the red blood cells within the one or more microfluidic channels 104 may be configured to measure transit speed or transit times of the red blood cells.

In some embodiments, the at least one processor 110 may determine a speed distribution of the red blood cells based at least on the measured transit speed or transit times, to indicate the severity of the hematologic disease in the blood sample. The speed distribution may comprise one or more speed distribution metrics including, but is not limited to, at least shape, outliers, average speed, maximum speed, standard deviation, and skewness. Further, the at least one processor 110 may analyze the generated sequence of digital holography images or videos using the AI/ML module 114 to track the red blood cells within the one or more microfluidic channels 104. In some embodiments, the quantification and characterization of the red blood cell deformability are configured to generate a score or relative indicator of a health status and/or indicate an efficacy of a medical treatment of the user based on the severity of a hematologic disease in the blood sample. In some embodiments, the at least one processor 110 may be configured to analyze the generated sequence of digital holographic images or videos are analyzed to assess the distribution of transit speeds of the red blood cells as they pass through the one or more microfluidic channels 104.

FIG. 9 illustrates an exemplary scenario 900 of the system 100 to determine severity of the hematologic disease i.e., sickle cell disease, in accordance with an example embodiment of the present disclosure. FIG. 9 is described in conjunction with FIGS. 1-8.

In some embodiments, the exemplary scenario 900 may comprise the at least one imaging device 106 as discussed above in conjunction with FIGS. 1-5. Further, the system 100 may comprise the at least one user device 118 that may be configured to receive the quantified deformability of the blood sample to display a report on a display device 902 of the at least one user device 118 related to a user's 904 health status. In some example embodiments, the at least one user device 118 and the display device 902 may be a smartphone, a tablet, a laptop, a personal computer (PC), a smart watch or any other device known in the art to display the report. In one example, the user 904 may receive the report in his/her user device, like the smartphone. In some embodiments, the report may comprise at least one score or relative indicator of the user's 904 health status and/or indicate an efficacy of a medical treatment of the user 904 based on the severity of the hematologic disease in the red blood cells. The system 100 may further transfer the report to the user 904, via the cloud 116. In some embodiments, the AI/ML module 114 may implement image analysis to generate information provided in the report entailing the details of the user's 904 health status.

As discussed above, the at least one processor 110 may be configured to analyze the generated sequence of digital holography images or videos using AI/ML module 114. The AI/ML module 114 may be configured to analyze the generated sequence of digital holography images or videos to quantify and characterize transit speeds of the red blood cells of the blood sample to generate a distribution of the transit speeds or times. The AI/ML module 114 may implement AI/ML algorithms to quantify deformability of the red blood cells. The AI/ML module 114 may track red blood cells within the one or more microfluidic channels 104. The red blood cells may deform within the one or more microfluidic channels 104. The quantification and characterization of the blood sample are configured to generate a score or relative indicator of a health status and/or indicate an efficacy of a medical treatment of the user based on the severity of the hematologic disease in the blood sample.

As discussed, the one or more speed distribution metrics may include, but is not limited to, one or more shapes, outliers, average speed, maximum speed, standard deviation, and skewness. It will be apparent that the sequence of digital holography images or videos may be acquired one or more times to assess deformability of red blood cells and determine severity of the hematologic diseases. In some embodiments, the bi-modal distribution indicates presence of young red blood cells due to short lifetime of diseased cells.

The present disclosure involves utilizing microfluidic channels and a digital holography technique to determine severity of the hematologic disease. The microfluidic channels may be coated/functionalized in order to mimic vascular conditions within the microfluidic channels. The images/videos are analyzed to quantify deformability of red blood cells flowing through the microfluidic channels. Therefore, a detailed report of severity of the hematologic disease, such as sickle cell disease, is provided to the user remotely. The present disclosure also provides a benefit of not labelling the cells, that is, the cells are unstained and untagged.

Many modifications and other embodiments of the disclosure set forth herein will come to mind to one skilled in the art to which the present disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A system, comprising:

one or more deformability devices having one or more microfluidic channels with at least one cross-sectional dimension smaller than a nominal thickness of a red blood cell, wherein the one or more microfluidic channels with the at least one cross-sectional dimension is configured to deform red blood cells of a blood sample that flow through the one or more microfluidic channels;

at least one digital holographic imager configured to generate a sequence of digital holography images or videos of the red blood cells of the blood sample that flow through the one or more microfluidic channels; and at least one processor operationally coupled to the at least one digital holographic imager and configured to:

receive the sequence of digital holography images or videos; and analyze the generated sequence of digital holography images or videos to quantify and characterize deformability of the red blood cells that transition through the one or more microfluidic channels.

2. The system of claim 1, wherein the one or more microfluidic channels have an interior surface that is coated with a plurality of endothelial cells.

3. The system of claim 1, wherein the one or more microfluidic channels comprise at least one inlet and at least one outlet, wherein the at least one inlet is configured to receive the blood sample and the at least one outlet is configured to discharge the red blood cells.

4. The system of claim 1, wherein to quantify and characterize deformability of the red blood cells within the one or more microfluidic channels, the at least one processor is further configured to measure transit speed or transit times of the red blood cells.

5. The system of claim 4, wherein a speed distribution of the red blood cells of the blood sample is determined based at least on the transit speed measured or transit times measured of the red blood cells to indicate a severity of a hematologic disease in the blood sample.

6. The system of claim 5, wherein the speed distribution comprises one or more distribution metrics including one or more of shape, outliers, average speed, maximum speed, standard deviation, and skewness.

7. The system of claim 5, wherein, to quantify and characterize the deformability of the red blood cells deformed, the at least one processor is further configured to generate a score or relative indicator of a health status or indicate an efficacy of a medical treatment based on the severity of the hematologic disease in the blood sample.

8. The system of claim 7, further comprising at least one user device, wherein the at least one user device is configured to receive a report related to the health status.

9. The system of claim 1, wherein the at least one digital holographic imager comprises a lensless in-line digital holography configuration to generate the sequence of digital holography images or videos.

10. The system of claim 1, wherein the at least one processor is further configured to analyze the generated sequence of digital holography images or videos using an Artificial Intelligence/Machine Learning module to track the red blood cells within the one or more microfluidic channels.

11. The system of claim 1, wherein the red blood cells are unstained and untagged.

12. A method, comprising:

deforming, with a deformability device, red blood cells of a blood sample flowing through one or more microfluidic channels of the deformability device, wherein the one or more microfluidic channels comprising at least one cross-sectional dimension smaller than a nominal thickness of a red blood cell;

generating, via at least one digital holographic imager, a sequence of digital holography images or videos of the red blood cells of the blood sample flowing through the one or more microfluidic channels; and analyzing, via at least one processor, the generated sequence of digital holography images or videos to quantify and characterize deformability of the red blood cells transiting through the one or more microfluidic channels.

13. The method of claim 12, wherein the one or more microfluidic channels have an interior surface that is coated with a plurality of endothelial cells.

14. The method of claim 12, wherein analyzing the generated sequence of digital holography images or videos to quantify and characterize deformability of the red blood cells within the one or more microfluidic channels comprises measuring transit speed or transit times of the red blood cells.

15. The method of claim 14, further comprising:

determining, via the at least one processor, a speed distribution of the red blood cells based at least in part on the transit speed measured or transit times measured of the red blood cells, to indicate a severity of a hematologic disease in the blood sample.

16. The method of claim 15, wherein the speed distribution comprises one or more distribution metrics including one or more of shape, outliers, average speed, maximum speed, standard deviation, and skewness.

17. The method of claim 12, wherein the at least one digital holographic imager comprises a lensless in-line digital holography configuration to generate the sequence of digital holography images or videos.

18. The method of claim 12, further comprising:

analyzing, via the at least one processor, the generated sequence of digital holography images or videos using an Artificial Intelligence/Machine Learning module to track the red blood cells within the one or more microfluidic channels.

19. The method of claim 12, wherein analyzing the generated sequence of digital holography images or videos to quantify and characterize deformability of the red blood cells includes generating a score or relative indicator of a health status or indicating an efficacy of a medical treatment based on a severity of a hematologic disease in the blood sample.

20. The method of claim 19, further comprising:

transmitting, to at least one user device, a report related to the health status.

* * * * *